US012685666B2

(12) United States Patent
Sayama et al.

(10) Patent No.: US 12,685,666 B2
(45) Date of Patent: Jul. 21, 2026

(54) CONDOM AND METHOD FOR MANUFACTURING SAME

(71) Applicant: OKAMOTO INDUSTRIES, INC., Tokyo (JP)

(72) Inventors: Yuuki Sayama, Tokyo (JP); Iwao Endo, Tokyo (JP)

(73) Assignee: Okamoto Industries, Inc., Tokyo (JP)

( * ) Notice: Subject to any disclaimer, the term of this patent is extended or adjusted under 35 U.S.C. 154(b) by 0 days.

(21) Appl. No.: 18/726,575

(22) PCT Filed: Jan. 6, 2023

(86) PCT No.: PCT/JP2023/000142
§ 371 (c)(1),
(2) Date: Jul. 3, 2024

(87) PCT Pub. No.: WO2023/132355
PCT Pub. Date: Jul. 13, 2023

(65) Prior Publication Data
US 2025/0073060 A1 Mar. 6, 2025

(30) Foreign Application Priority Data

Jan. 6, 2022 (JP) ................................. 2022-000957

(51) Int. Cl.
*A61F 6/04* (2006.01)
(52) U.S. Cl.
CPC ............ *A61F 6/04* (2013.01); *A61F 2240/00* (2013.01)
(58) Field of Classification Search
CPC ........ A61F 2006/043; A61F 6/02; A61F 6/04; A61F 2006/044; A61F 2006/046;
(Continued)

(56) References Cited

U.S. PATENT DOCUMENTS

| | | | |
|---|---|---|---|
| 4,795,425 A * | 1/1989 | Pugh | A61F 6/04 604/349 |
| 5,102,405 A * | 4/1992 | Conway | A61F 6/04 604/352 |

(Continued)

FOREIGN PATENT DOCUMENTS

| JP | 57-32015 U1 | 2/1982 |
|---|---|---|
| JP | S59-53022 U1 | 4/1984 |

(Continued)

OTHER PUBLICATIONS

International Search report PCT/JP2023/000142 dated Mar. 20, 2023 (pp. 1-2).

(Continued)

*Primary Examiner* — Kari K Rodriquez
(74) *Attorney, Agent, or Firm* — Millen, White, Zelano & Branigan P.C.; William F. Nixon

(57) ABSTRACT

A decline in viscosity of a first lubricant due to perspiration, pressure of insertion, thrusting, and the like during coitus is prevented and, a high adherence with a penis is obtained. In a condom, lubricants are added to a condom main body, wherein the lubricants include a first lubricant and a second lubricant, the first lubricant is made of a silicone oil having a higher viscosity than a viscosity of the second lubricant and is provided on an inner peripheral surface of at least a tip part of the condom main body, and the second lubricant is provided on an outer peripheral surface of at least the tip part of the condom main body.

2 Claims, 2 Drawing Sheets

(58) Field of Classification Search
CPC .......... A61F 2006/047; A61F 2006/048; A61F 2006/049

See application file for complete search history.

(56) References Cited

U.S. PATENT DOCUMENTS

| | | | | |
|---|---|---|---|---|
| 5,513,654 | A * | 5/1996 | Delson | A61F 6/04 427/2.3 |
| 5,549,924 | A * | 8/1996 | Shlenker | A61F 6/04 427/407.1 |
| 5,679,399 | A * | 10/1997 | Shlenker | A61F 6/04 427/407.1 |
| 5,878,747 | A * | 3/1999 | Enomoto | A61L 31/10 128/918 |
| 6,536,438 | B1 * | 3/2003 | Kakonyi | A61F 6/04 128/918 |
| 7,086,403 | B2 * | 8/2006 | Harrison | A61K 9/0034 128/918 |
| 2003/0021903 | A1 * | 1/2003 | Shlenker | A01N 25/10 427/407.1 |
| 2009/0107513 | A1 * | 4/2009 | Zedalis | A61F 6/04 427/2.3 |
| 2018/0153800 | A1 * | 6/2018 | Memin | A61K 9/0014 |
| 2021/0009331 | A1 * | 1/2021 | Platt | A61F 6/04 |
| 2025/0073060 | A1 | 3/2025 | Sayama et al. | |

FOREIGN PATENT DOCUMENTS

| | | | |
|---|---|---|---|
| JP | S5953022 | U | 4/1984 |
| JP | H5-21924 | U1 | 3/1993 |
| JP | H06213467 | A | 8/1994 |
| JP | 2001327522 | A | 11/2001 |
| JP | 2008-093283 | A | 4/2008 |
| JP | 7588102 | B2 | 11/2024 |
| WO | 2002045573 | A2 | 6/2002 |
| WO | 2023132355 | A1 | 7/2023 |

OTHER PUBLICATIONS

Office Action issued in Japanese Patent Application No. 2022-000957 dated Aug. 6, 2024 (pp. 1-4).

Written Opinion of the International Search Authority dated Mar. 20, 2023, issued in corresponding PCT/JP2023/000142.

Malaysian Office Action dated Aug. 13, 2025 issued in corresponding application PI2024003550.

* cited by examiner (a)

(b)

CONDOM AND METHOD FOR MANUFACTURING SAME

TECHNICAL FIELD

The present invention relates to a condom that is a male contraceptive having lubricants added thereto and to a method for manufacturing the condom.

BACKGROUND ART

Conventionally, as a condom of this type, there is a condom in which a jelly is applied to an inside of a glans-covering part and a silicone oil is applied to the entire condom to ensure lubrication performance of an outside surface of the condom and lubrication performance when the condom is worn (for example, refer to PTL 1).

The jelly contains a polyol-based compound and a carboxy vinyl polymer and improves adherence by bringing the glans of a user and the inside of the glans-covering part of the condom into close contact with each other via the jelly.

CITATION LIST

Patent Literature

[PTL 1] Japanese Patent Application Laid-open No. 2008-093283

SUMMARY OF INVENTION

Problems to be Solved by Invention

However, in PTL 1, since the polyol-based compound contained in the jelly is water soluble, viscosity of the jelly drops when the jelly is mixed with moisture in the form of perspiration or the like and severely impairs the adherence between the glans of the user and the inside of the glans-covering part of the condom. Such a decline in adherence problematically makes the condom susceptible to shifting during coitus, hence increases risks of being taken off and the like.

Furthermore, since the carboxy vinyl polymer contained in the jelly has superior thixotropy (a property of losing viscosity when subjected to a certain force), there is a problem in that the viscosity of the jelly declines due to pressure of insertion, thrusting, and the like during coitus, making the condom susceptible to shifting and being taken off during coitus, and further increasing risks.

Means for Solving the Problems

In order to solve such problems, a condom according to the present invention is a condom comprising a condom main body and lubricants applied to the condom main body, wherein the lubricants include a first lubricant and a second lubricant, the first lubricant is made of a silicone oil having a higher viscosity than a viscosity of the second lubricant and is provided on an inner peripheral surface of at least a tip part of the condom main body, and the second lubricant is provided on an outer peripheral surface of at least the tip part of the condom main body.

In addition, in order to solve such problems, a method for manufacturing a condom according to the present invention is a method for manufacturing a condom including a condom main body and lubricants applied to the condom main body, the method including: a winding step of winding the condom main body to form the condom main body into a flat shape; and a filling step of supplying the lubricants to the wound condom main body, wherein in the filling step, an inner peripheral surface of at least a tip part of the condom main body is filled with a first lubricant, an outer peripheral surface of at least the tip part of the condom main body is filled with a second lubricant, and the first lubricant is made of a silicone oil having a higher viscosity than a viscosity of the second lubricant.

DESCRIPTION OF EMBODIMENTS

Hereinafter, an embodiment of the present invention will be described in detail with reference to the drawings.

Figure 1:
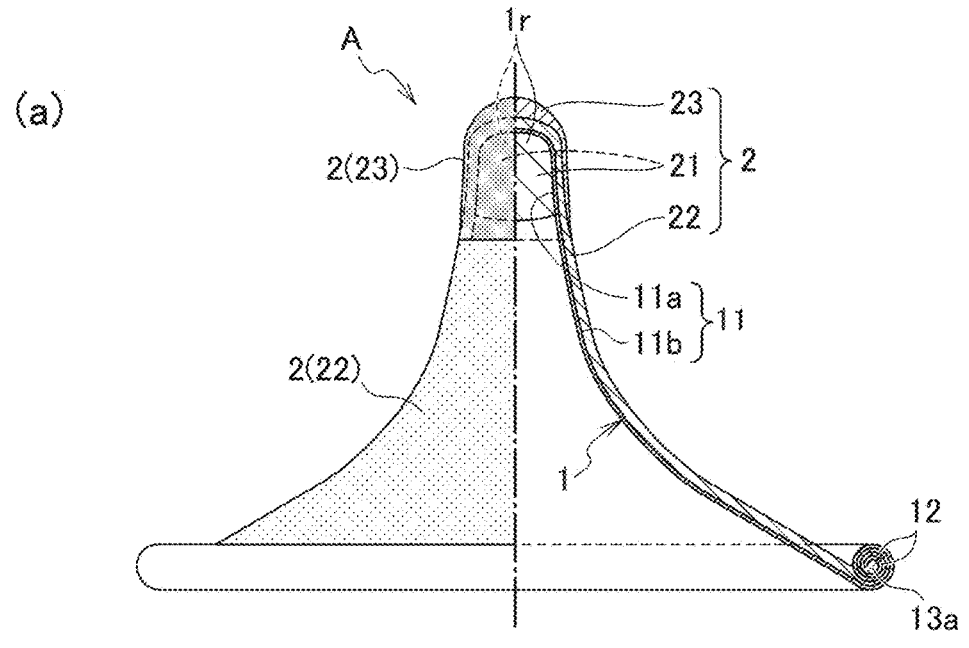
FIG. 1 is an explanatory diagram showing an overall configuration of a condom according to an embodiment of the present invention in which (a) is a partially cutaway front view in a wound state immediately after manufacture and (b) is a partially cutaway front view in an unwound state immediately after manufacture.
Figure 1:
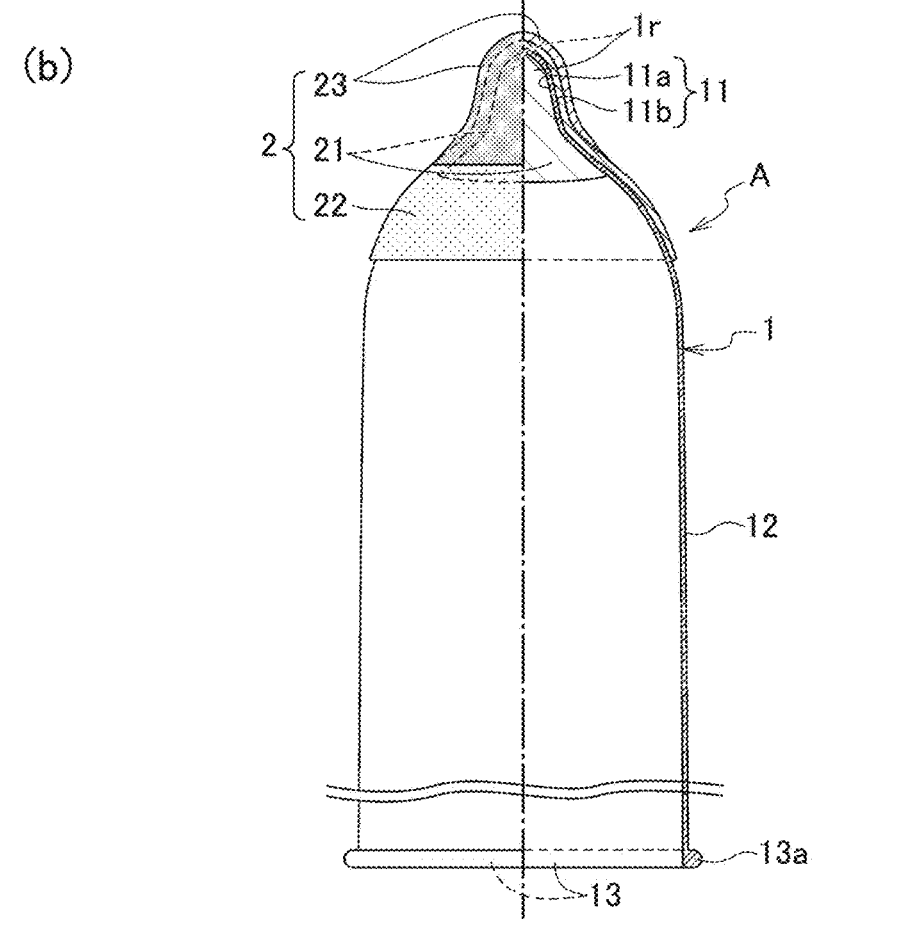
Figure 2:
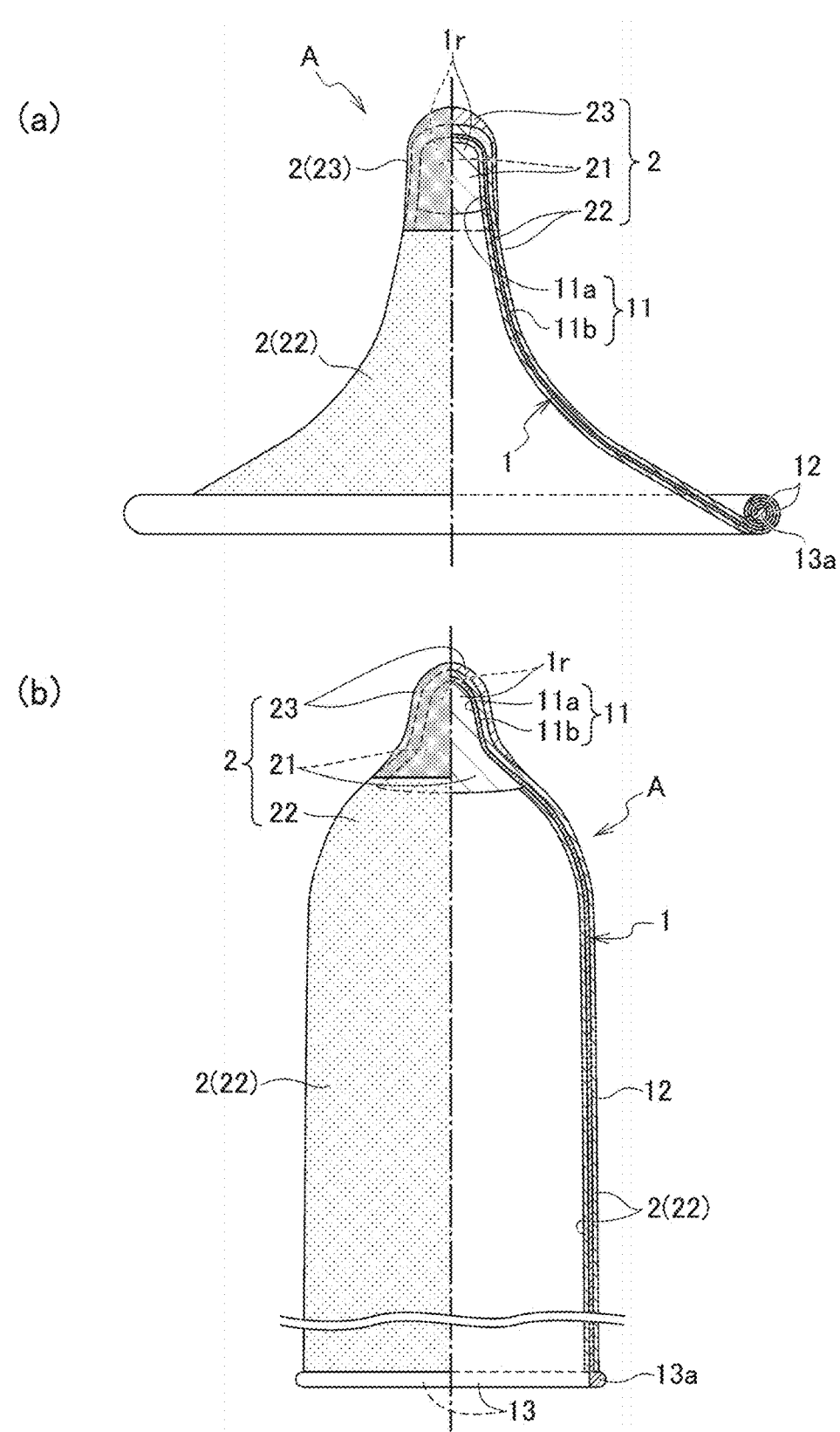
FIG. 2 shows states after a predetermined period of time has elapsed from immediately after manufacture in which (a) is a partially cutaway front view in a wound state and (b) is a partially cutaway front view in an unwound state.

As shown in FIGS. 1 and 2, a condom A according to the embodiment of the present invention is a contraceptive to be worn on the male sexual organ (penis) for the purpose of preventing unwanted pregnancies and transmission of venereal diseases and in which lubricants 2 are added (provided) by being applied with respect to a condom main body 1.

More specifically, the condom A according to the embodiment of the present invention includes, as main constituent elements, a first lubricant 21 which is provided on an inner side of at least a tip of the condom main body 1 and a second lubricant 22 which is provided on an outer side of at least the tip part of the condom main body 1.

Furthermore, a third lubricant 23 is preferably provided on an outer side of the second lubricant 22.

The condom main body 1 is formed of an elastic material such as natural rubber (latex), polyurethane, isoprene rubber, silicone rubber, and nitrile rubber in a thin bag shape corresponding to the shape of the penis.

The condom main body 1 includes a tip part 11 which opposes a tip portion (glans part) of the penis, a body part 12 which opposes an intermediate portion of the penis, and an opening 13 which opposes a root portion of the penis. Wide varieties of shapes, thicknesses, diameter sizes, length sizes, and the like of the condom main body 1 are prepared in accordance with respective purposes.

In the illustrated case as a specific example of the condom main body 1, the shape of the condom main body 1 is formed in a cylindrical shape with an approximately same shape in a length direction as a whole, a liquid retention part $1r$ is included in the tip part 11, and a ring part $13a$ is included in the opening 13.

In addition, as another example, although not illustrated, the condom main body 1 can be changed to a size other than the illustrated example such as forming the condom main body 1 so that the diameter size partially differs in accordance with an outer shape of the penis or the diameter size gradually increases from a base end side toward a tip side of the condom main body 1. Furthermore, as described in Japanese Patent Application Laid-open No. 2008-093283 and the like, the liquid retention part 1r need not be present at the tip of the condom main body 1.

The lubricants 2 are made of a silicone oil and includes the first lubricant 21, the second lubricant 22, and the third lubricant 23 with different viscosities in correspondence with different portions of the condom main body 1. Since the silicone oil is oil-based, the silicone oil is not water-soluble and has a property of not mixing with moisture such as perspiration. However, when attached to the body or the like, the silicone oil can be readily washed off with detergent or the like.

The first lubricant 21 is set to a higher viscosity than the viscosities of the second lubricant 22 and the third lubricant 23 and is filled along an inner peripheral surface 11a of the tip part 11 by supplying a predetermined amount of high-viscosity silicone oil toward the inner peripheral surface 11a of at least the tip part 11 of the condom main body 1.

The second lubricant 22 is set to a lower viscosity than the viscosities of the first lubricant 21 and the third lubricant 23 and is filled along an outer peripheral surface 11b of the tip part 11 by supplying a predetermined amount of low-viscosity silicone oil toward the outer peripheral surface 11b of at least the tip part 11 of the condom main body 1 and the second lubricant 22 is applied in a film state.

The third lubricant 23 is set to a lower viscosity than the viscosity of the first lubricant 21 and a higher viscosity than the viscosity of the second lubricant 22 and is filled along the second lubricant 22 by supplying a predetermined amount of medium-viscosity silicone oil toward an outer side of the second lubricant 22 on the outer peripheral surface 11b of the tip part 11 of the condom main body 1 and the third lubricant 23 is applied in a film state.

Furthermore, as the first lubricant 21 and the third lubricant 23 of the lubricants 2, an impermeable silicone oil which does not permeate between the outer surface and the inner surface of the condom main body 1 in a thickness direction is used. Moreover, as the second lubricant 22, a permeable silicone oil which permeates between the outer surface and the inner surface of the condom main body 1 in a wound state in a thickness direction is preferably used.

Respective viscosities and fill amounts (application amounts) of the first lubricant 21, the second lubricant 22, and the third lubricant 23 provided in respective portions of the condom main body 1 are set to appropriate values so that appropriate adherence and lubrication performance are obtained in each portion of the condom main body 1.

Note that viscosities of the first lubricant 21, the second lubricant 22, and the third lubricant 23 are measured according to a test method stipulated in JIS K 2283 "Crude petroleum and petroleum products-Determination of kinematic viscosity and calculation of viscosity index from kinematic viscosity". A measurement temperature was set to "25° C.". The unit "cP (centipoise=1 mPa·s)" was adopted as a unit of viscosity.

When the viscosity of the first lubricant 21 is less than approximately 5,000 cP, an appropriate adherence is not obtained between the inner peripheral surface 11a of at least the tip part 11 of the condom main body 1 and the glans part. In addition, when the viscosity of the first lubricant 21 exceeds approximately 20,000 cP, fluidity of the first lubricant 21 declines dramatically and the first lubricant 21 can no longer extend and slide with ease between the inner peripheral surface 11a of at least the tip part 11 of the condom main body 1 and the glans part. Therefore, the viscosity of the first lubricant 21 is preferably set to 5,000 to 20,000 cP.

When the viscosity of the second lubricant 22 is less than approximately 100 cP, a risk arises that the second lubricant 22 may be absorbed into the body, and the second lubricant 22 cannot be used and is therefore not preferable. In addition, when the viscosity of the second lubricant 22 exceeds approximately 300 cP, fluidity dramatically declines and the second lubricant 22 hardly penetrates into a gap of the body part 12 of the wound condom main body 1. Therefore, the viscosity of the second lubricant 22 is preferably set to 100 to 300 cP.

When the viscosity of the third lubricant 23 is less than approximately 500 cP, the third lubricant 23 is no longer held on the outer peripheral surface 11b of the tip part 11 of the condom main body 1 and a function (effect) of reducing resistance during insertion to the female sexual organ (vagina) decreases. In addition, when the viscosity of the third lubricant 23 exceeds approximately 2,000 cP, fluidity dramatically declines and the third lubricant 23 can no longer readily extend between the outer peripheral surface 11b of the tip part 11 of the condom main body 1 and a surface of the vagina. Therefore, the viscosity of the third lubricant 23 is preferably set to 500 to 2,000 cP.

In other words, a viscosity ratio of the first lubricant 21, the second lubricant 22, and the third lubricant 23 is set to 5,000 to 20,000:100 to 300:500 to 2,000=50 to 200:1 to 3:5 to 20. Specifically, the viscosity ratio of the lubricants is preferably set to first lubricant:second lubricant:third lubricant=50:1:5. In this case, the viscosity of the first lubricant 21 is approximately 10,000 cP, the viscosity of the second lubricant 22 is approximately 200 cP, and the viscosity of the third lubricant 23 is approximately 1,000 cP.

When the fill amount of the first lubricant 21 is less than approximately 100 mg, the first lubricant 21 does not sufficiently entirely extend between the inner peripheral surface 11a of at least the tip part 11 of the condom main body 1 and the glans part and an appropriate adherence is not obtained. In addition, when the fill amount of the first lubricant 21 exceeds approximately 1,000 mg, the first lubricant 21 more readily leaks from the opening 13 when wearing the condom main body 1 on the penis. Therefore, the fill amount of the first lubricant 21 is preferably set to 100 to 1,000 mg.

When the fill amount of the second lubricant 22 is less than approximately 100 mg, the second lubricant 22 does not entirely extend between the inner surface of the body part 12 of the condom main body 1 and an intermediate portion of the penis and an appropriate lubrication performance (moistness and smoothness) is not obtained. In addition, when the fill amount of the second lubricant 22 exceeds approximately 1,000 mg, the second lubricant 22 more readily leaks when wearing the condom main body 1 on the penis. Therefore, the fill amount of the second lubricant 22 is preferably set to 100 to 1,000 mg.

When the fill amount of the third lubricant 23 is less than approximately 100 mg, the third lubricant 23 does not entirely extend between the outer peripheral surface 11b of the tip part 11 of the condom main body 1 and the female sexual organ (surface of the vagina) and an appropriate lubrication performance (moistness and smoothness) is not obtained. In addition, when the fill amount of the third lubricant 23 exceeds approximately 1,000 mg, the third lubricant 23 more readily leaks when inserting the condom main body 1 into the vagina. Therefore, the fill amount of the third lubricant 23 is preferably set to 100 to 1,000 mg.

In other words, a fill amount ratio of the first lubricant 21, the second lubricant 22, and the third lubricant 23 is set to 100 to 1,000:100 to 1,000:100 to 1,000=1 to 10:1 to 10:1 to 10. Specifically, the fill amount ratio of the lubricants is preferably set to first lubricant:second lubricant:third lubricant=1:1:1. In this case, the fill amount of the first lubricant 21 is approximately 550 mg, the fill amount of the second lubricant 22 is approximately 550 mg, and the fill amount of the third lubricant 23 is approximately 550 mg.

[Manufacturing Method]

In the method for manufacturing the condom A according to the embodiment of the present invention, manufacturing processes of the condom main body 1 include, as main steps: an immersion molding step using a forming mold (not illustrated) fabricated in a same shape as an outer shape of the penis; a drying step of the condom main body 1 having been subjected to immersion molding; a winding step of winding the dried condom main body 1 and forming the condom main body 1 into a flat shape; and a packaging step of encapsulating the wound condom main body 1.

A filling step of supplying the lubricants 2 to the wound condom main body 1 is preferably included between the winding step and the packaging step. As a method of supplying the lubricants 2 to the condom main body 1, preferably, each of predetermined amounts of the first lubricant 21, the second lubricant 22, and the third lubricant 23 is injected to respective portion of the condom main body 1 by a pump, a nozzle, or the like from a supply source such as a tank storing the first lubricant 21, the second lubricant 22, and the third lubricant 23.

In the filling step of the lubricants 2, the first lubricant 21, the second lubricant 22, and the third lubricant 23 are sequentially filled in the wound state of the condom main body 1 as shown in FIG. 1 at (a).

In the packaging step after the filling step, the condom main body 1 filled with the first lubricant 21, the second lubricant 22, and the third lubricant 23 is encapsulated in a sealed state with a package material (not illustrated).

Therefore, as shown in FIG. 1 at (b), permeation of the second lubricant (permeable silicone oil) 22 with respect to the body part 12 of the condom main body 1 is insufficient immediately after filling with the first lubricant 21, the second lubricant 22, and the third lubricant 23 (immediately after manufacture) even when the condom main body 1 is unwound.

By comparison, once a predetermined period of time has elapsed after filling with the first lubricant 21, the second lubricant 22, and the third lubricant 23 (a time point prior to sales of product), the permeable silicone oil to become the second lubricant 22 permeates from the outer surface to the inner surface of the condom main body 1 in the wound state of the condom main body 1 shown in FIG. 2 at (a).

Therefore, in the unwound state (upon use) of the condom main body 1 shown in FIG. 2 at (b), the permeable silicone oil to become the second lubricant 22 has permeated from the outer surface to the inner surface of the body part 12 of the condom main body 1.

With the condom A and the method for manufacturing the condom A according to the embodiment of the present invention described above, the inner peripheral surface 11*a* of at least the tip part 11 of the condom main body 1 is provided with the first lubricant 21 made of a silicone oil with a higher viscosity than the viscosity of the second lubricant 22. Accordingly, in a state where the condom main body 1 is worn on the male sexual organ (penis), the high-viscosity first lubricant 21 is retained between the glans part and the inner peripheral surface 11*a* of the tip part 11 which oppose each other.

Since the silicone oil that constitutes the first lubricant 21 is not water soluble, the silicone oil does not mix with moisture such as perspiration, and the viscosity does not change (decline) even when subjected to certain force.

Therefore, a decline in viscosity of the first lubricant 21 due to perspiration, pressure of insertion, thrusting, and the like during coitus can be prevented and a high adherence with the penis can be obtained.

As a result, compared to conventional jellies that contain a water-soluble polyol-based compound and carboxy vinyl polymer with superior thixotropy, the inner peripheral surface 11*a* of the tip part 11 of the condom main body 1 continuously adheres to the glans part using the first lubricant 21 and a strong grip force can be maintained during coitus. Accordingly, shifting of the tip part 11 with respect to the glans part, an occurrence of wrinkles, penetration of air, and the like can be reliably prevented. Therefore, damage and removal of the tip part 11 due to friction during coitus can be prevented and a higher level of safety can be achieved.

Furthermore, due to a decrease in a sense of discomfort caused by shifting, stiffening, or catching of the condom main body 1 and an increased sense of adherence, the user (male) during coitus can experience a renewed sense of togetherness between the penis and the female sexual organ (vagina) and appreciate improved sexual sensitivity.

In particular, preferably, the third lubricant 23 is provided on an outer side of the second lubricant 22 and the third lubricant 23 is made of a silicone oil with a higher viscosity than the viscosity of the second lubricant 22.

In this case, the outer peripheral surface 11*b* of at least the tip part 11 of the condom main body 1 is provided with the third lubricant 23 made of a silicone oil with a higher viscosity (medium viscosity) than the viscosity of the second lubricant 22 so as to sandwich the second lubricant 22. Accordingly, during insertion of the penis wearing the condom main body 1, the third lubricant 23 with high viscosity is pooled between the female sexual organ (surface of the vagina) and the outer peripheral surface 11*b* of the tip part 11 which oppose each other.

Since the medium-viscosity silicone oil that constitutes the third lubricant 23 is not water soluble, the silicone oil does not mix with moisture such as female secretion and the viscosity does not change (decline) even when subjected to certain force.

Therefore, a decline in viscosity of the third lubricant 23 due to female secretion, pressure of insertion, thrusting, and the like can be prevented and frictional resistance with the surface of the vagina can be reduced.

As a result, the users (male and female) can experience a smoother sense of insertion during coitus.

Furthermore, since pain for the female during coitus decreases and a sense of discomfort due to shifting, stiffening, or catching of the condom main body 1 also decreases, the female can appreciate improved sexual sensitivity.

Furthermore, the second lubricant 22 preferably permeates the condom main body 1.

In this case, by providing the second lubricant 22 on the outer peripheral surface 11*b* of at least the tip part 11 of the condom main body 1 during manufacture when the condom main body 1 is wound, the second lubricant 22 permeates into a gap of the wound condom main body 1 (body part 12) and permeates from the outer peripheral surface 11*b* of the tip part 11 and the outer surface side of the body part 12 of the condom main body 1 to the inner peripheral surface 11*a* and the inner surface side of the body part 12.

For this reason, by unwinding the condom main body 1 when wearing the condom main body 1 on the penis, the second lubricant 22 spreads from the outer peripheral surface 11*b* and the inner peripheral surface 11*a* of the tip part 11 of the condom main body 1 toward a body part outer peripheral surface 12*b* and a body part inner peripheral surface 12*a*, respectively.

Therefore, the condom main body 1 can be readily unwound when wearing the condom main body 1 and both lubrication performance of the inside surface of the body part 12 with respect to the surface of the penis and the lubrication performance of the outside surface of the body part 12 with respect to the surface of the vagina during coitus can be secured.

As a result, when the condom main body 1 is worn on the penis, a smoother wearing sensation is obtained. From the female's perspective, since pain during coitus further decreases and a sense of discomfort due to shifting, stiffening, or catching of the condom main body 1 also decreases, a further improved sexual sensitivity can be appreciated.

EXAMPLES

Hereinafter, examples of the present invention will be described.

Examples 1 to 9 and Comparative Examples 1 to 9

In each of Examples 1 to 9 shown in Table 1 and Comparative examples 1 to 9 shown in Table 2, a condom main body was filled with the lubricants (the first lubricant, the second lubricant, and the third lubricant) described in the tables and evaluation samples of a same size were fabricated.

Examples 1 to 9 and Comparative examples 1 to 9 share a same configuration in which the condom main bodies are made of natural rubber (latex) and formed in a cylindrical shape with a thickness of 0.05 mm and a liquid retention part in a tip part thereof.

In Examples 1 to 9 each, 100 to 1,000 mg of the first lubricant with a viscosity of 5,000 to 20,000 cP was filled, 100 to 1,000 mg of the second lubricant with a viscosity of 100 to 300 cP was filled, and 100 to 1,000 mg of the third lubricant with a viscosity of 500 to 2,000 cP was filled.

Specifically, in Example 1, 550 mg of the first lubricant with a viscosity of 5,000 cP was filled, 550 mg of the second lubricant with a viscosity of 200 cP was filled, and 550 mg of the third lubricant with a viscosity of 1,000 cP was filled.

In Example 2, 550 mg of the first lubricant with a viscosity of 20,000 cP was filled, and the viscosities and fill amounts of the second lubricant and the third lubricant were the same as in Example 1.

In Example 3, 100 mg of the first lubricant with a viscosity of 10,000 cP was filled, 550 mg of the second lubricant with a viscosity of 200 cP was filled, and 550 mg of the third lubricant with a viscosity of 1,000 cP was filled.

In Example 4, 1,000 mg of the first lubricant with a viscosity of 10,000 cP were filled, and the viscosities and fill amounts of the second lubricant and the third lubricant were the same as in Example 3.

In Example 5, 550 mg of the first lubricant with a viscosity of 10,000 cP was filled, 550 mg of the second lubricant with a viscosity of 200 cP was filled, and 550 mg of the third lubricant with a viscosity of 1,000 cP was filled.

In Example 6, 550 mg of the first lubricant with a viscosity of 10,000 cP was filled, 550 mg of the second lubricant with a viscosity of 200 cP was filled, and 550 mg of the third lubricant with a viscosity of 500 cP was filled.

In Example 7, 550 mg of the third lubricant with a viscosity of 2,000 cP was filled, and the viscosities and fill amounts of the first lubricant and the second lubricant were the same as in Example 6.

In Example 8, 550 mg of the first lubricant with a viscosity of 10,000 cP was filled, 550 mg of the second lubricant with a viscosity of 200 cP was filled, and 100 mg of the third lubricant with a viscosity of 1,000 cP was filled.

In Example 9, 1,000 mg of the third lubricant with a viscosity of 1,000 cP was filled, and the viscosities and fill amounts of the first lubricant and the second lubricant were the same as in Example 8.

On the other hand, in Comparative examples 1 to 9 each, less than 100 mg or more than 1,000 mg of the first lubricant with a viscosity lower than 5,000 cP or higher than 20,000 cP was filled, less than 100 mg or more than 1,000 mg of the second lubricant with a viscosity lower than 100 cP or higher than 300 cP was filled, and less than 100 mg or more than 1,000 mg of the third lubricant with a viscosity lower than 500 cP or higher than 2,000 cP was filled.

Specifically, Comparative example 1 differs from Example 1 and Example 2 in that 550 mg of the first lubricant with a viscosity of 4,000 cP was filled, and the viscosities and fill amounts of the second lubricant and the third lubricant were the same as in Example 1 and Example 2.

Comparative example 2 differs from Example 1 and Example 2 in that 550 mg of the first lubricant with a viscosity of 21,000 cP was filled, and the viscosities and fill amounts of the second lubricant and the third lubricant were the same as those in Example 1 and Example 2.

Comparative example 3 differs from Example 3 and Example 4 in that 50 mg of the first lubricant with a viscosity of 10,000 cP was filled, and the viscosities and fill amounts of the second lubricant and the third lubricant were the same as those in Example 3 and Example 4.

Comparative example 4 differs from Example 3 and Example 4 in that 1,100 mg of the first lubricant with a viscosity of 10,000 cP was filled, and the viscosities and fill amounts of the second lubricant and the third lubricant were the same as those in Example 3 and Example 4.

Comparative example 5 differs from Example 6 and Example 7 in that 550 mg of the third lubricant with a viscosity of 400 cP were filled, and the viscosities and fill amounts of the first lubricant and the second lubricant were the same as those in Example 6 and Example 7.

Comparative example 6 differs from Example 6 and Example 7 in that 550 mg of the third lubricant with a viscosity of 2,100 cP were filled, and the viscosities and fill amounts of the first lubricant and the second lubricant were the same as those in Example 6 and Example 7.

Comparative example 7 differs from Example 8 and Example 9 in that 50 mg of the third lubricant with a viscosity of 1,000 cP were filled, and the viscosities and fill amounts of the first lubricant and the second lubricant were the same as those in Example 8 and Example 9.

Comparative example 8 differs from Example 8 and Example 9 in that 1,100 mg of the third lubricant with a viscosity of 1,000 cP were filled, and the viscosities and fill amounts of the first lubricant and the second lubricant were the same as those in Example 8 and Example 9.

Comparative example 9 differs from Example 5 and the like in that the second lubricant was not filled at all, and the viscosities and fill amounts of the first lubricant and the third lubricant were the same as those in Example 5 and the like.

[Evaluation Criteria]

Evaluation results (sense of adherence, sense of insertion, grip feel, and unwinding feel) shown in Table 1 and Table 2 were based on the following indexes.

"Sense of adherence" is a test for verifying adherence of Examples 1 to 9 and Comparative examples 1 to 9 with respect to the glans part of the penis.

The evaluation of the "sense of adherence" was performed by a control test using an artificial vagina in which a plurality of (20) men wearing the evaluation samples according to Examples 1 to 9 and Comparative examples 1 to 9 respectively performed insertion and thrusting a plurality of times with respect to an artificial vagina under the same conditions and evaluated the adherence with respect to the glans part on a four-point scale.

The evaluation results of the "sense of adherence" represented evaluations of A: excess or deficiency of the first lubricant never occurred and adherence with the glans part was extremely high, B: excess or deficiency of the first lubricant did not occur, and adherence with the glans part was high, C: adherence with the glans part was slightly lacking but not an issue, and D: inferior insertion performance due to deficiency of the first lubricant or leakage due to excess of the first lubricant.

"Sense of insertion" is a test for verifying insertion performance of Examples 1 to 9 and Comparative examples 1 to 9 with respect to the vagina.

The evaluation of the "sense of insertion" was performed by a control test using an artificial vagina in which a plurality of (20) men each wearing the evaluation samples according to Examples 1 to 9 and Comparative examples 1 to 9 performed insertion with respect to an artificial vagina under the same conditions and evaluated the insertion performance on a four-point scale.

The evaluation results of the "sense of insertion" represented evaluations of A: excess or deficiency of the third lubricant never occurred and insertion performance was extremely favorable, B: excess or deficiency of the third lubricant did not occur and insertion performance was favorable, C: insertion performance was slightly lacking but not an issue, and D: inferior adherence due to deficiency of the third lubricant or leakage due to excess of the third lubricant.

"Grip feel" is a test for verifying shifting of Examples 1 to 9 and Comparative examples 1 to 9 with respect to the penis.

The evaluation of the "grip feel" was performed by a control test using an artificial vagina in which a plurality of (20) men each wearing the evaluation samples according to Examples 1 to 9 and Comparative examples 1 to 9 performed insertion and thrusting a plurality of times with respect to an artificial vagina under the same conditions and evaluated shifting with respect to the penis on a three-point scale.

The evaluation results of the "grip feel" represented evaluations of B: excess or deficiency of the second lubricant never occurred and shifting never occurred, C: slight shifting occurred but not an issue, and D: shifting due to deficiency of the second lubricant or leakage due to excess of the second lubricant.

"Unwinding feel" is a test for verifying unwinding performance of Examples 1 to 9 and Comparative examples 1 to 9 with respect to the penis.

The evaluation of the "unwinding feel" was performed by a control test in which a plurality of (20) men each wearing the evaluation samples according to Examples 1 to 9 and Comparative examples 1 to 9 performed a test of unwinding the evaluation samples along the penis a plurality of times under the same conditions and evaluated the unwinding performance on a three-point scale.

The evaluation results of the "unwinding feel" represented evaluations of B: unwinding can be performed smoothly without inclusion of air between the evaluation sample and the penis, C: while slight inclusion of air between the evaluation sample and the penis occurs, the evaluation sample can be unwound without incident, and D: the evaluation sample cannot be smoothly unwound due to inclusion of air between the penis and the evaluation sample or the like.

"Comprehensive evaluation" represents a comprehensive evaluation on a four-point scale based on the evaluation results of the "sense of adherence", the "sense of insertion", the "grip feel", and the "unwinding feel" described above.

The evaluation results of the "comprehensive evaluation" represented evaluations of A: optimal, B: good, C: slightly lacking but within an acceptable range, and D: unsuitable.

TABLE 1

| | | Examples | | | | | | | | |
|---|---|---|---|---|---|---|---|---|---|---|
| | | 1 | 2 | 3 | 4 | 5 | 6 | 7 | 8 | 9 |
| First lubricant | Viscosity (cP) | 5,000 | 20,000 | 10,000 | 10,000 | 10,000 | 10,000 | 10,000 | 10,000 | 10,000 |
| | Fill amount (mg) | 550 | 550 | 100 | 1000 | 550 | 550 | 550 | 550 | 550 |
| Second lubricant | Viscosity (cP) | 200 | 200 | 200 | 200 | 200 | 200 | 200 | 200 | 200 |
| | Fill amount (mg) | 550 | 550 | 550 | 550 | 550 | 550 | 550 | 550 | 550 |
| Third lubricant | Fill amount (mg) | 1,000 | 1,000 | 1,000 | 1,000 | 1,000 | 500 | 2,000 | 1,000 | 1,000 |
| | Fill amount (mg) | 550 | 550 | 550 | 550 | 550 | 550 | 550 | 100 | 1,000 |
| Evaluation result | Sense of adherence | C | B | C | B | A | A | A | A | A |
| | Sense of insertion | A | A | A | A | A | C | B | C | B |
| | Grip feel | C | B | C | C | B | C | B | C | C |
| | Unwinding | B | B | B | B | B | 8 | B | B | B |
| | Comprehensive evaluation | B | B | B | B | A | B | B | B | B |

TABLE 2

| | | Comparative examples | | | | | | | | |
|---|---|---|---|---|---|---|---|---|---|---|
| | | 1 | 2 | 3 | 4 | 5 | 6 | 7 | 8 | 9 |
| First lubricant | Viscosity (cP) | 4,000 | 21,000 | 10,000 | 10,000 | 10,000 | 10,000 | 10,000 | 10,000 | 10,000 |
| | Fill amount (mg) | 550 | 550 | 550 | 1,100 | 550 | 550 | 550 | 550 | 550 |
| Second lubricant | Viscosity (cP) | 200 | 200 | 200 | 200 | 200 | 200 | 200 | 200 | Second lubricant is absent |
| | Fill amount (mg) | 550 | 550 | 550 | 550 | 550 | 550 | 550 | 550 | |
| Third lubricant | Viscosity (cP) | 1,000 | 1,000 | 1,000 | 1,000 | 400 | 2,100 | 1,000 | 1,000 | 1,000 |
| | Fill amount (mg) | 550 | 550 | 550 | 550 | 550 | 550 | 50 | 1,100 | 550 |
| Evaluation result | Sense of adherence | D | D | D | D | A | A | A | A | A |
| | Sense of insertion | A | A | A | A | D | D | D | D | A |
| | Grip feel | C | C | C | C | C | C | C | C | B |
| | Unwinding feel | B | B | B | B | B | B | B | B | D |
| | Comprehensive evaluation | D | D | D | D | D | D | D | D | D |

[Evaluation Result]

A comparison between Examples 1 to 9 and Comparative examples 1 to 9 revealed that favorable results were obtained by Examples 1 to 9 in terms of all of the sense of adherence, the sense of insertion, the grip feel, the unwinding feel, and the comprehensive evaluation.

As is apparent from the evaluation result, Examples 1 to 9 were proved to be condoms that combine superior sense of adherence, sense of insertion, grip feel, and unwinding feel. In particular, Example 5 was proved to be a condom that combines particularly superior sense of adherence, sense of insertion, grip feel, and unwinding feel.

By contrast, Comparative examples 1 to 9 produced a poor evaluation result in any of the sense of adherence, the sense of insertion, the grip feel, and the unwinding feel.

Specifically, in Comparative example 1, the glans part did not sufficiently adhere to the inner peripheral surface of at least the tip part of the condom main body due to the viscosity of the first lubricant being excessively low and produced a poor evaluation result in terms of the sense of adherence.

In Comparative example 2, the first lubricant did not sufficiently extend between the inner peripheral surface of at least the tip part of the condom main body and the glans part due to the viscosity of the first lubricant being excessively high and produced a poor evaluation result in terms of the sense of adherence.

In Comparative example 3, the first lubricant did not sufficiently spread between the inner peripheral surface of at least the tip part of the condom main body and the glans part due to an insufficient fill amount of the first lubricant, and produced a poor evaluation result in terms of the sense of adherence. From these evaluation results, even when the first lubricant was not filled, a poor evaluation result in terms of the sense of adherence was produced in a similar manner to Comparative example 3.

In Comparative example 4, due to an excessive fill amount of the first lubricant, the first lubricant leaked out from the opening during wearing of the condom main body on the penis and produced a poor evaluation result in terms of the sense of adherence.

In Comparative example 5, due to the viscosity of the third lubricant being excessively low, sufficient lubrication performance (moistness and smoothness) was not created between the outer peripheral surface of the tip part of the condom main body and the surface of the vagina and produced a poor evaluation result in terms of the sense of insertion.

In Comparative example 6, due to the viscosity of the third lubricant being excessively high, the third lubricant did not sufficiently extend between the outer peripheral surface of the tip part of the condom main body and the surface of the vagina and produced a poor evaluation result in terms of the sense of insertion.

In Comparative example 7, due to an insufficient fill amount of the third lubricant, the third lubricant did not sufficiently spread between the outer peripheral surface of the tip part of the condom main body and the surface of the vagina and produced a poor evaluation result in terms of the sense of insertion. From these evaluation results, even when the third lubricant was not filled, a poor evaluation result in terms of the sense of insertion was produced in a similar manner to Comparative example 7.

In Comparative example 8, due to an excessive fill amount of the third lubricant, the third lubricant leaked out during insertion of the condom main body into the vagina and produced a poor evaluation result in terms of the sense of insertion.

In Comparative example 9, due to the absence of the second lubricant, a poor evaluation result in terms of the unwinding feel was produced. From these evaluation results, even when the fill amount of the second lubricant was less than 100 mg and insufficient, the second lubricant did not sufficiently spread between the inside surface of the body part of the condom main body and the intermediate portion of the penis and a poor evaluation result in terms of the unwinding feel was produced in a similar manner to Comparative example 9. In addition, when the fill amount of the second lubricant exceeded 1,000 mg and was excessive, the second lubricant leaked out during insertion of the condom main body into the vagina and produced a poor evaluation result.

Furthermore, although not shown in Comparative examples 1 to 9, when the viscosity of the second lubricant is lower than 100 cP, there is a risk that the second lubricant may be absorbed by the human body, and even when the viscosity of the second lubricant was higher than 300 cP, the second lubricant did not sufficiently spread entirely between the inside surface of the body part of the condom main body and the intermediate portion of the penis and a poor evaluation result in terms of the unwinding feel was produced in a similar manner to Comparative example 9.

While a configuration including a condom main body made of natural rubber (latex) was used as a common configuration in Examples 1 to 9 and Comparative examples 1 to 9 described above, the configuration is not restrictive, and polyurethane, isoprene rubber, silicone rubber, nitrile rubber, or the like may be used in place of natural rubber (latex). Furthermore, while a configuration formed in a cylindrical shape with medium thickness and a liquid retention part in a tip part was used as a common configuration in Examples 1 to 9 and Comparative examples 1 to 9 described above, the configuration is not restrictive, and a configuration with a thickness that is thinner than medium thickness or thicker than medium thickness, a configuration in which a diameter size of the condom main body is formed so as to partially differ in conformance with the outer shape of the penis, a configuration in which the shape of the condom main body gradually increases from the base end side toward the tip side, a configuration in which the diameter of the condom main body gradually increases from the base end side toward the tip side, a configuration without a liquid retention part, or the like may be adopted.

Even in those cases, evaluation results similar to those of Examples 1 to 9 were produced.

[Reference Signs List]

| A: | Condom | 1: | Condom main body |
|---|---|---|---|
| 11: | Tip part | 11a: | Inner peripheral surface |
| 11b: | Outer peripheral surface | 2: | Lubricant |
| 21: | First lubricant | 22: | Second lubricant |
| 23: | Third lubricant | | |

The invention claimed is:

1. A condom comprising:
a condom main body; and
lubricants applied to the condom main body, wherein
the lubricants include a first lubricant, a second lubricant, and a third lubricant,
the first lubricant is made of a silicone oil having a higher viscosity than a viscosity of the second lubricant and is provided on an inner peripheral surface of at least a tip part of the condom main body, and
the second lubricant is provided on an outer peripheral surface of at least the tip part of the condom main body and the second lubricant is permeable from an outer surface to an inner surface of the condom main body, and
the third lubricant is made of a silicone oil having a higher viscosity than the viscosity of the second lubricant and is provided on an outer side of the second lubricant.

2. A method for manufacturing a condom including a condom main body and lubricants applied to the condom main body, the method comprising:
a winding step of winding the condom main body to form the condom main body into a flat shape; and
a filling step of supplying the lubricants to the wound condom main body,
wherein in the filling step, an inner peripheral surface of at least a tip part of the condom main body is filled with a first lubricant, an outer peripheral surface of at least the tip part of the condom main body is filled with a second lubricant, after the second lubricant being filled, the outer peripheral surface of at least the tip part of the condom main body is filled with a third lubricant made of a silicone oil with a higher viscosity than a viscosity of the second lubricant so as to sandwich the second lubricant, the first lubricant is made of a silicone oil having a higher viscosity than the viscosity of the second lubricant, and the second lubricant is permeable from an outer surface to an inner surface of the condom main body.

* * * * *